United States Patent
Toumi (10) Patent No.: US 7,749,390 B2
(45) Date of Patent: Jul. 6, 2010

(54) SEMI-CONTINUOUS CHROMATOGRAPHIC METHOD AND CORRESPONDING DEVICE FOR THE SEPARATION OF BINARY AND MULTI-COMPONENT MIXTURES

(75) Inventor: Abdelaziz Toumi, Düsseldorf (DE)

(73) Assignee: Bayer Technology Services, GmbH, Leverkusen (DE)

(*) Notice: Subject to any disclaimer, the term of this patent is extended or adjusted under 35 U.S.C. 154(b) by 172 days.

(21) Appl. No.: 11/916,057

(22) PCT Filed: Jun. 3, 2006

(86) PCT No.: PCT/EP2006/005341

§ 371 (c)(1),
(2), (4) Date: Jun. 9, 2008

(87) PCT Pub. No.: WO2006/131286

PCT Pub. Date: Dec. 14, 2006

(65) Prior Publication Data

US 2009/0194482 A1    Aug. 6, 2009

(30) Foreign Application Priority Data

Jun. 9, 2005   (DE) .................. 10 2005 026 486

(51) Int. Cl.
*B01D 15/08* (2006.01)
(52) U.S. Cl. .............. 210/659; 210/656; 210/198.2
(58) Field of Classification Search ........... 210/635, 210/656, 659, 662, 672, 198.2
See application file for complete search history.

(56) References Cited

U.S. PATENT DOCUMENTS

| | | | |
|---|---|---|---|
| 2,621,149 A | 12/1952 | Scott et al. | |
| 2,985,589 A | 5/1961 | Broughton et al. | |
| 3,796,657 A * | 3/1974 | Pretorius | 210/635 |
| 5,102,553 A | 4/1992 | Kearney et al. | |
| 5,139,680 A * | 8/1992 | Tarnopolsky | 210/656 |
| 5,770,087 A * | 6/1998 | Reuter | 210/657 |
| 6,602,420 B2 | 8/2003 | Kearney et al. | |
| 6,712,973 B2 | 3/2004 | Adam et al. | |
| 6,805,799 B2 | 10/2004 | Ma | |
| 2006/0186048 A1* | 8/2006 | Tan | 210/656 |

FOREIGN PATENT DOCUMENTS

WO    01 87924    11/2001

OTHER PUBLICATIONS

Jensen T. B. et al: Novel Simulated Moving-Bed Method for Reduce Solvent Consumption. Journal of Chromatography, Elsevier Science Publishers B.V. Amsterdam, NL, vol. 873, No. 2, Mar. 2000, pp. 149-162, XP004202666, ISSN: 0021-9673.

(Continued)

*Primary Examiner*—Ernest G Therkorn
(74) *Attorney, Agent, or Firm*—Norris McLaughlin & Marcus, P.A.

(57) ABSTRACT

The invention relates to a semi-continuous chromatographic method for the separation of binary and multi-component mixtures and corresponding devices.

4 Claims, 5 Drawing Sheets

OTHER PUBLICATIONS

Hilbrig F. et al: Continuous Annular Chromatography. Journal of Chromatography. Journal of Chromatography B: Biomedical Sciences & Applications, Elsevier, Amsterdamn, NL, vol. 790. No. 1-2, Jun. 25, 2003, pp. 1-15 XP004426785, ISSN: 1570-0232.

Hoheisel, Werner; Nanoparticles in Diagnostics and Therapeutics (an Overview), Foundation of the Naotechnology Section, Dechema, Frankfurt, Nov. 11, 2004, p. 1-p. 38.

Gao, Xiaohu, et al: In Vivo Cancer Targeting and Imaging With Semiconductor Quantum Dots; Nature Biotechnology, vol. 22, No. 8, Aug. 2004, pp. 969-975.

Wu, Xingyong, et al: Immunofluorescent Labeling of Cancer Marker Her2 and Other Cellular Targets With Semiconductor Quantum Dots; Nature Biotechnology, Jan. 2003, vol. 21, pp. 41-46.

Kompe, Karsten, et al. Green-Emitting CEPO4: TB/LAPO4 Core-Shell Nanoparticles With 70% Photoluminescence Quantum Yield; Angew. Chem. Int. Ed. 2003, 42, pp. 5513-5516.

Heer, Stephan, et. al. Blue, Green, and Red Upconversion Emission From Lanthanide-Doped LUPO4 and YBPO4 Nanocrystals in a Transparent Colloidal Solution, Angew. Chem. Int. Ed 2003, 42, pp. 3179-3182.

Franz, Karl A. et al. Luminescent Material, Wiley-VCH Verlag GMBH & Co., KGAA, Jun. 15, 2000, pp. 1-48.

Protein Fluorescence, Chapter 11.

Clay Bosewell, UPT and Other SMB Providers Make Large-Scale Chromatograpny Viable, Chemical Market Reporter, 2001, vol. 259, pp. 1-15.

Baudouin et. al., Desucrage Des Egouts et Des Melasses, Industries Alimentaires et Agric . . . , 2003, vol. 120, pp. 42-48., English Abstract.

Costesson, D., et. al., Improved Simulated Moving Bed Process for Purifying Sugar Solution, Zuckerindustrie-Berlin, vol. 125, 2000 pp. 333-335.

Imamoglu, Sabine; Simulated Moving Bed Chromatogrpahy (SMB) for Application in Bioseparation, Advances in Biochemical Engineering, Biotechnology, vol. 76, Springer-Verlag Berlin Heidelberg 2002, pp. 227-231.

Juza, Markus, et. al., Simulated Moving-Bed Chromatography and Its Application to Chirotechnology, Trends in Biotechnology, vol. 18, Mar. 2000, pp. 108-118.

Lutin F., et al., Process Improvements With Innovative Technologies in the Starch and Sugar Industries, Elsevier Science B.V., Desalination 148, (2002) pp. 121-124.

Negawa, Masakazu, et al., Optical Resolution by Simulated Moving-Bed Adsorption Technology, Journal of Chromatography, 590 (1992), pp. 113-117, Elsevier Science Publication B.V., Amsterdam.

Schramm, Henning, et. al., Simulated Moving Bed Process With Cyclic Modulation of the Feed Concentration, Journal of Chromatography A, 1006 (2003) pp. 77-86.

Schulte, Michael, et. al., Preparative Enantioseparation by Simulated Moving Bed Chromatogrpahy, Journal of Chromatography A, 906 (2001) pp. 399-416.

* cited by examiner

Y direction

X direction

Fig 8

Y direction

SEMI-CONTINUOUS CHROMATOGRAPHIC METHOD AND CORRESPONDING DEVICE FOR THE SEPARATION OF BINARY AND MULTI-COMPONENT MIXTURES

This is a 371 of PCT/EP2006/005341 filed 6 Jun. 2006 (international filing date).

The present invention relates to a chromatographic quasi-continuous process for separating binary and multisubstance mixtures and to the corresponding apparatus.

BACKGROUND OF THE INVENTION

Chromatographic processes enable the separation and purification of chemical, fine-chemical, biological and pharmaceutical products. Compared to other thermal separating processes, they have the particular advantage that they can be performed at moderate and hence product-protective temperatures (M. Juza, M. Mazzotti and M. Morbidelli, Trends in Biotechnology, 18, 2000, pages 108-118; S. Imamoglu, Advances in Biochemical Engineering/Biotechnology, 76, 2002, pages 211-231). In many applications, especially in the lifescience sector, the high purity requirements attached to the end products can additionally often only be achieved with the aid of chromatographic processes (M. Schulte and J. Strube, Journal of Chromatography A 906, 2001, pages 399-416).

The so-called batchwise process is widespread. It is particularly flexible and technically comparatively simple to build. In successive cycles, a finite pulse of the substance mixture to be separated is in each case applied to the chromatographic column. Thereafter, elution is effected with one or more solvents. The different components are adsorbed to different degrees as the mixture flows through the chromatographic column, are separated as a consequence and are fractionated at the outlet of the column. This is followed by a phase of fixed bed regeneration. A new batch cannot be started until either the preceding batch has ended or the most strongly adsorbable component of the preceding batch has migrated sufficiently far in order not to be overtaken by the more weakly adsorbable component. The batchwise process therefore generally takes a lot of time to purify a given amount of product.

In addition to the batchwise method, there exist continuous alternatives which find use principally in medium scale and in industrial scale production (B. Clay, Chemical Market Report 259, 2001, page 15). They generally have lower solvent consumption and allow higher productivity. The principle of continuous countercurrent chromatography is known from M. Negawa and F. Shoji, Journal of Chromatography 590, 1992, pages 113-117. Suitable units for performing continuous countercurrent chromatography, especially the so-called simulated moving bed (SMB) units, are described, for example, in U.S. Pat. No. 2,621,149 B; U.S. Pat. No. 2,985,589 B and are commercially available.

In general, in an SMB unit, a plurality of individual columns are bonded to form a closed circuit. At one point in the circuit, feed is supplied, which generally comprises a binary mixture (A+B). At a further point in the circuit, pure solvent is supplied. The internal concentration profile which arises for the A+B mixture is established after a startup phase. The more weakly adsorbing component (A) is drawn off in the so-called raffinate outlet, while the more strongly adsorbable component (B) is obtained in the extract outlet. In the course of operation of the SMB unit, the inlets and outlets are relayed via valves, for example single valves, multiway valves, valve blocks, flaps or rotary valves, periodically, but not necessarily simultaneously, in the direction of liquid flow, such that a countercurrent motion of liquid stream and stationary phase appears to arise. The zones identified in the SMB process between the particular inlets and outlets have the following roles in the overall separation process:

Zone I: Desorption of the strongly adsorbable component (A),

Zone II: Desorption of the weakly adsorbable component (B),

Zone III: Adsorption of the strongly adsorbable component (A),

Zone IV: Adsorption of the weakly adsorbable component (B).

In the patent literature, a series of developments of the simulated moving bed process can be found, mainly with the aim of achieving better separating performances and/or of extending the process to multisubstance separations.

In the patent U.S. Pat. No. 6,712,973 B, for example, an asynchronous switching of the inlet and outlet sites is undertaken, which gives rise to additional degrees of freedom for influencing the mean zone lengths. The patent U.S. Pat. No. 5,102,553 B patents a method in which the volume flows can be altered during a switching period, as a result of which the product withdrawal, both in the extract and in the raffinate, can be adjusted better to the course of the axial concentration profile with time. H. Schramm, M. Kaspereit and A. Seidel-Morgenstern, Journal of Chromatography A 1006, 2003, pages 77-86 additionally propose modulation of the feed concentrations, which leads to a significant increase in the productivity. The economic advantage over the conventional SMB method is, in this case, however, greatly restricted by the solubility limits of the substance mixture in the eluent. U.S. Pat. No. 6,602,420 B finally describes a method for purifying sucrose with the aid of the SMB process, in which the so-called displacement effect is utilized. The displacement effect here describes the property of the components of highly concentrated solutions to mutually displace one another owing to interaction mechanisms, which results in an additional separating effect.

Further processes known in the patent literature are ISMB and SSMB. In the so-called improved SMB process (ISMB), as the main difference from the conventional SMB process, the input and output are decoupled from the recycling (D. Costesson, G. Rearick and M. Kearne, Zucker-industrie 125, 2000, pages 333-335). Once the feed and eluent have been supplied and the raffinate and extract have been removed, pure recycling takes place. Subsequently, the ports are switched synchronously one column further in flow direction. The energy requirement of the recycling phase is a dominating factor in the overall costs of industrial scale units. This can be reduced in the ISMB process, since the recycling pump does not deliver permanently (F. Lutin, M. Bailly and D. Bar, Desalination 148, 2002, pages 121-124). The sequential SMB process (SSMB) is designed for the recovery of several fractions of a substance mixture and is used exclusively in the sugar industry (S. Baudouin and X. Lancrenon, Industries Alimentaires et Agricoles, 120, 2003, pages 42-48). Similarly to the SMB process, several columns are arranged in a closed circuit. In contrast to the conventional SMB method, the input and output are configured in a discontinuous manner. Furthermore, feed can be supplied at several points in the circuit. The product streams can likewise be collected at any time at the outlet of every column. The recycling of impure fractions can be effected either in the same column or in an adjacent column. SSMB corresponds to an intelligent arrangement of a plurality of batch columns, is basically a batchwise process and only partly utilizes the advantages of a simulated countercurrent. What additionally results is a complex scheduling problem which has to be solved for the optimal operation of such units.

The patent U.S. Pat. No. 6,805,799 presents a new "SMB focusing" method, with whose aid multisubstance mixtures can be separated in an "SMB unit". In this case, a gradient profile is achieved by establishing differences, for example, in salt content or pH from zone to zone. As a result, only one component should elute at the outlet of each zone. Feed is applied in the first zone and the components are obtained gradually according to their elution power in the particular zones. Similarly to the SSMB process, the countercurrent effect is not utilized here. This structure corresponds, if anything, to a coupled operation of a plurality of batch columns. The use of this method is restricted to separation problems in which an additional external influencing factor, for example (salt content or pH), can be found on the separating action. Furthermore, a significant gradient has to be formed.

The conventional SMB process and all continuous extensions known to date (VARICOL, PowerFeed, ModiCon, ISMB, etc.) can in principle only be used for binary separating tasks. Even the recovery of one component from a mixture is possible only when the latter is the most strongly or the most weakly adsorbable component. This is a disadvantage compared to batchwise operation, which thus enables more flexible operation. This is the reason why the majority of industrial uses are in the batchwise operation.

Owing to the fact that the conventional SMB process can divide a multisubstance mixture only into two fractions, its application to multisubstance separations entails the utilization of a plurality of SMB units which are arranged, for example, in a cascade. Patent U.S. Pat. No. 6,602,420 B describes, for example, the industrial recovery of sucrose with a cascade of two SMB units. However, this means a considerable capital investment. It is more economically favorable to operate a single SMB unit in which the individual separating steps are performed successively in time until the multisubstance mixture has been separated into its individual constituents. However, this is associated with high production complexity and time demand. In this case, SMB technology, however, loses the advantages over batchwise operation with regard to productivity and solvent consumption which have been praised to date.

In addition to batch chromatography, in the separation of multisubstance mixtures, so-called annular chromatography has also become established (Finke et al., J. Agric. Food Chem., 50, 2002, pages 185-201; F. Hilbrig, Journal of Chromatography B, 790, 2003, pages 1-17). In annular chromatography, the feed is supplied at a fixed location to a rotating column, while eluent is introduced to the remaining circumference. As a result of the rotation of the chromatographic column, bands form and elute at different angles. It is thus possible to separate a multisubstance mixture into its individual constituents. In annular chromatography, the separation is effected, in spite of the radial motion, mainly in axial direction. The annular chromatography therefore corresponds to a batch process with many columns arranged in a circle. At the same time, very high amounts of solvent are required. Difficulties in the distribution of the solution at the top and the accumulation of the products at the bottom of a CAC (continuous annular chromatography) unit are known, and uniform input and output of the components to and from a rotating column constitute an engineering challenge which has not been solved satisfactorily to date for a large unit with correspondingly high throughput. However, the possibility of continuously separating a multisubstance mixture is advantageous.

There is therefore an urgent need for a chromatographic process which enables the separation of binary and multisubstance mixtures, and the process should be employable economically in a single unit.

SUMMARY OF THE INVENTION

The present invention therefore provides a chromatographic quasi-continuous process for separating binary and multisubstance mixtures in a unit which consists of a plurality of individual columns bonded to one another in a direction X in a circle, characterized in that a two-dimensional separation is achieved by a) in step 1 of the period p, supplying the feed in a column m and supplying an eluent stream in the direction Y to the other columns, b) in step 2 of the period p, flowing an eluent stream through the bonded columns in the direction X and forming a circulation stream, c) in step 1 of the period p+1, supplying further feed in the column m+1 and supplying further eluent stream in direction Y to the other columns, d) in step 2 of the period p+1, again flowing an eluent stream through the bonded columns in the direction X and forming a circulation stream, e) repeating a) to d) continuously.

The process according to the invention builds on the principle of simulated countercurrent chromatography. Surprisingly, modification of the SMB process, in which the components migrate to diagonal bands in a similar manner to annular chromatography, achieves the effect that these components can be separated in a single apparatus. The process according to the invention also combines batchwise operation with SMB technology, which enables quasi-continuous separation of multisubstance mixtures. Owing to this combination, the novel process profits both from the flexibility of the batchwise process and from the higher productivity and lower solvent consumption of the SMB process. Furthermore, the adsorbent is utilized better compared to the customary batchwise operation. A process design concept for this purpose can be realized more simply than in the case of the conventional SMB process. The process according to the invention is suitable for the separation of binary mixtures and is thus capable of replacing the conventional SMB process. Unlike the conventional SMB process, it can also be used to separate multisubstance mixtures.

DETAILED DESCRIPTION

A particular embodiment of the process according to the invention is illustrated with reference to FIG. 1.

BRIEF DESCRIPTION OF THE DRAWINGS

Figure 1:
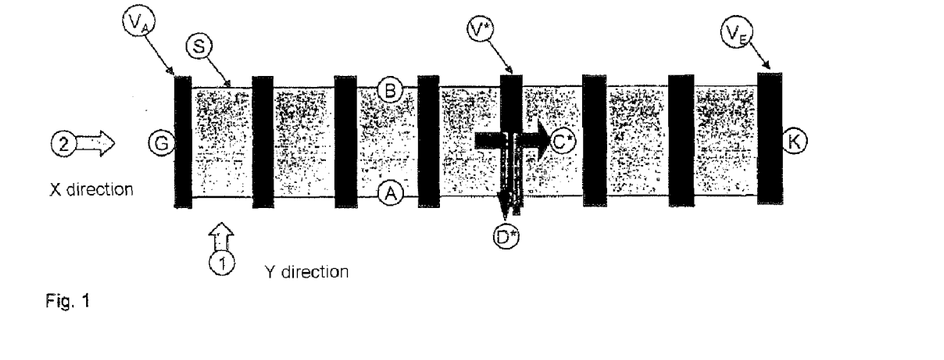
FIG. 1: Illustrates the base elements of an apparatus for the novel process

FIG. 1 shows the base elements of an apparatus for the process according to the invention, without being restricted thereto.

A plurality of chromatographic columns (S*), at least 2, preferably from 3 to 12, are connected in series. In radial Y direction (1), the bottom is charged along the complete width and forms the column inlet (A*), opposite which is the column outlet (B*). Each column is connected to the neighboring column in X direction by a specific distributor (V*) which has a distributor inlet (C*) and a distributor outlet (D*). The chromatographic circuit is closed by virtue of the end of the last column being connected to the start of the first column by a distributor $V_A$. Alternatively, the end of the last column is connected to the start of the first column by two distributors $V_E$ around the line K in the sequence $V_E$–K–$V_A$.

The chromatographic columns (S*) have, like an SMB column in the X direction, two lateral frits and filters. In addition, in the Y direction, two further frits and filters enable flow in the Y direction. Each column is filled with a stationary phase which, according to the separation problem, may be a normal, reversed, chiral, ion exchange or polymer phase. They are preferably packed as follows: the lower and the lateral frits and filters are installed first, the solid phase is filled from the top, preferably in the slurry method, and compressed by a hydraulically driven plunger or a liquid jet. Thereafter, the upper frit and the filter are installed.

In the period p, in step 1 (=injection phase), feed is supplied into the column $S_m$ through the feed inlet $A_m$; all other columns receive fresh eluent. At this time, all distributors (V*) are closed in X direction, such that the liquid applied leaves the column (S*) at the column outlet (B*). The outlet (B*) of each column can be connected here to all product vessels via fractionating valves. During the injection phase, the volume flow of each column can be adjusted independently. In this direction, the process is basically operated as a batchwise process. The volume flows should be adjusted here such that the particular target component is obtained in the desired purity and yield.

In the second step, separation is effected along the X direction (2) by supplying fresh solvent at the distributor inlet ($C_n$) of a given distributor ($V_n$), where, typically, m≧n. At the distributor outlet ($D_n$) of the same distributor ($V_n$), the circulation stream is removed. V. is open in X direction; all other distributors (V*) are open in X direction and thus enable a circulation stream through all columns. The overall concentration profile is conveyed in X direction.

At the distributor outlet ($D_n$), two situations can arise:
1. either pure solvent is discharged, which can be used further,
2. or the most easily adsorbable components are discharged, which can be passed into the corresponding product vessel.

This process thus corresponds to a skillful combination of the SMB and batchwise operation in a single apparatus, with the two methods effectively being passed through in alternation. The components migrate, as the illustrations which follow show, on different transverse tracks similarly to annular chromatography. The separation is effected here along two coordinates, which constitutes a fundamental difference from the annular and from the traditional chromatographic processes known to date. It is thus a true two-dimensional chromatographic process. The trajectory along which the tracks of the different components form can be influenced by volume flows established in radial and axial direction.

It is the task of the process design, depending on the mixture present and its thermodynamic properties, to configure the separating process such that only the components desired in each case can be obtained at the upper outlet (B*) of a given column (S*). The separation in the axial direction X is similar to the conventional SMB process, although it takes place without supply of feed. Therefore, this step can be designed in a relatively simple manner compared to the conventional SMB process. The volume flow can be established such that, at the end of the period, the column ($S_n$) charged with fresh eluent is regenerated completely, i.e. such that only pure solvent leaves the column.

The correct values for the volume flows are determined with reference to a model-based design calculation or experimentally.

Figure 2:
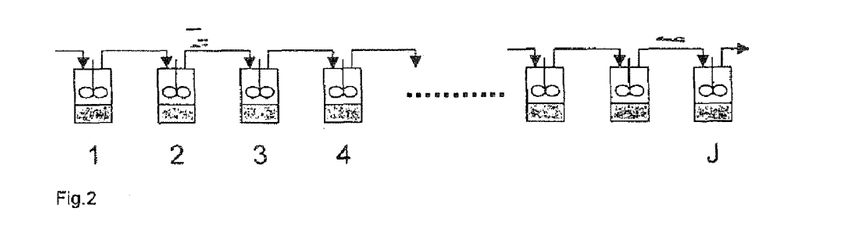
FIG. 2: Illustrates a plate model of a chromatographic column

In order to be able to understand and analyze the dynamic behavior of this process, the following mathematical model has been constructed. Each column is divided both in the axial and radial direction into plates in which a thermodynamic equilibrium between liquid and solid phase is assumed. This plate model, which is shown graphically in FIG. 2 in axial direction, very accurately reproduces the dynamic behavior of chromatographic separations and enables a close-to-reality study of the dynamic properties. The number of plates is a measure of the hydrodynamic efficiency and is determined with reference to the van-Deemter equation (Guiochon, G. 2002, Journal of Chromatography A, 965, 129-161):

$$J\{,K\} = \frac{B\{,H\}}{HETP}, \; HETP = A + Bu \; \text{and} \; u = \frac{Q}{A\varepsilon_{ext}}.$$

HETP is the Height Equivalent to Theoretical Plate, a measure of the fluid-dynamic efficiency of a chromatographic column, and is determined experimentally with reference to pulse experiments.

This gives rise to the following equation in axial X direction when the mass balance around one plate is considered:

$$C_i^{j-1,k} = C_i^{j,k} + \frac{T_0^J}{J}\frac{\partial C_i^{j,k}}{\partial t} + \frac{1-\varepsilon_{ext}}{\varepsilon_{ext}}\frac{T_0^J}{J}\frac{\partial \overline{C}_i^{j,k}}{\partial t},$$
$$i = 1, \ldots, n_{sp}; j = 1, \ldots, J; k = 1, \ldots, K$$

Analogously thereto, the following equation can be compiled in radial Y direction:

$$C_i^{j,k-1} = C_i^{j,k} + \frac{T_0^K}{K}\frac{\partial C_i^{j,k}}{\partial t} + \frac{1-\varepsilon_{ext}}{\varepsilon_{ext}}\frac{T_0^K}{K}\frac{\partial \overline{C}_i^{j,k}}{\partial t},$$
$$i = 1, \ldots, n_{sp}; j = 1, \ldots, J; k = 1, \ldots, K$$

in this context, $C_i^{j,k}$ describes the concentration in the liquid phase of the component k in the (i,j) plate, where i states the horizontal position (axial X direction) and j the vertical position (radial Y direction). $\overline{C}_i^{j,k}$ is in turn the corresponding concentration in the solid phase. $n_{sp}$ corresponds to the number of components. Between the solid and liquid phase, there is an adsorption equilibrium which is described in general terms by the following so-called isotherm equation:

$$\overline{C}_i^{j,k} = f(C_1^{j,k}, C_2^{j,k}, \ldots, C_{n_{sp}}^{j,k}),$$

Many separations follow a linear adsorption law. This is especially the case for highly dilute solutions. They are characterized by the so-called Henry coefficients:

$$\overline{C}_i^{j,k} = H_i C_i^{j,k}.$$

$T_0$ is the retention time and corresponds to the time taken by an unadsorbable substance to pass through the chromatographic column in the particular axial or radial direction. $\epsilon_{ext}$ finally describes the porosity of the packing.

This model describes chromatographic separations very accurately, as has been illustrated impressively in many publications (including Ludemann-Hombourger, O. and Nicoud, R.-M, 2000, Separation Science and Technology, 35, 1829-1862). The mathematical model can additionally serve to design the process.

Whether one or the other operating mode arises depends on the selection of the volume flows and the adsorption properties of the component to be separated.

The columns (S*) are flowed through in two different directions, preferably mutually perpendicular directions X (2) and Y (1).

The columns may be configured geometrically, either as cylindrical part-rings (2 columns give rise to half-rings) or square plates. When the columns are part-rings, the last distributor $V_E$ is dispensed with, since the end of the last column can be connected directly to the first distributor $V_A$, which gives rise to a cylindrical overall structure. For the high-pressure range of 20 to 200 bar, preference is given to cylindrical pressure-resistant shapes, while square columns find use in the low-pressure range.

Between the columns, in axial X direction, are disposed the distributors (V*) which fulfill the following functions:

1. The radial concentration profile which arises along the Y direction (1) in a chromatographic column (S*) should, in the course of flow through the column in X direction (2), be able to be transported to the neighboring column without great mixing effects.
2. Each distributor (V*) should, in the course of flow through the columns, in X direction (2), allow both the supply of a fresh eluent stream (through C*) into the circulation stream and the removal of the circulation stream (through D*).
3. The distributors (V*) should, in the course of flow through the columns, in Y direction (1), delimit the chromatographic columns from one another in hydrodynamic terms (circulation stream and D* connected), such that each column can be charged with its own defined radial volume flow.

Figure 3:
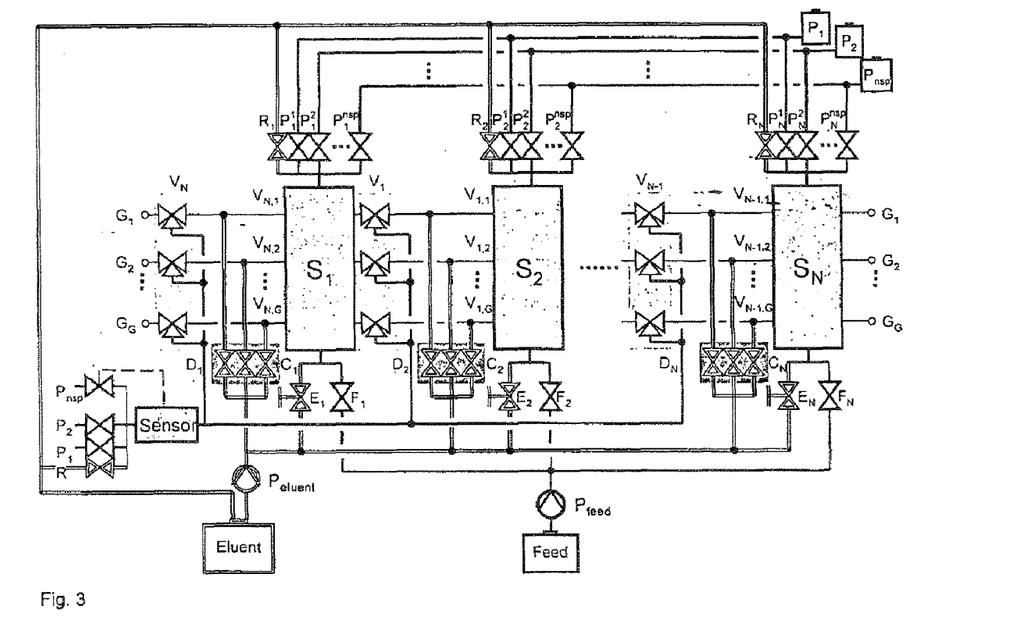
FIG. 3: Illustrates the construction of the overall system with valves

FIG. 3 shows a particular embodiment of the apparatus with overall construction of the overall system including periphery, consisting of pumps, valves and vessels.

N columns are connected in series. Moreover, a general multisubstance mixture with nsp components (nsp≧2) is assumed. Each column is divided along the radial Y direction into equidistant or into gradually finer G ranges. The distributor connects each G region g of the column m to the G region g of the column m+1, such that the concentration profile of the column m is passed on to the column m+1. In each region, the liquid is collected, then passed through a combination of barrier valves (v*), which form the distributor V*, either to the following column or to the distributor outlet (D*). Fresh eluent can be added to the circulation stream via the distributor inlet (C*), a simple valve. The eluent at the outlet of the distributor (D*) is as far as possible reused, in which case it can optionally be analyzed with the aid of a detector and fractionated correspondingly.

In radial Y direction, feed or eluent is applied to the lower inlets of the columns. In this case, the feed can be passed simultaneously to several columns. Preference is given to applying feed to a column in such a way that pure switching valves ($F_1$-$F_N$) are used. In contrast, control valves for the eluent input ($E_1$-$E_N$) are envisaged, which allows the eluent volume flow in radial Y direction of each column to be specified independently. Alternatively, instead of the control valves for the eluent inlet, delivery pumps can be used. The discharge of the column can either be passed through the fractionating valves $P^1$-$P^{nsp}$ into one of the product vessels or, according to R, be fed into the eluent vessel. A waste vessel can additionally be provided in order to discard incorrect cut fractions (not shown in FIG. 3 for reasons of clarity).

Figure 4:
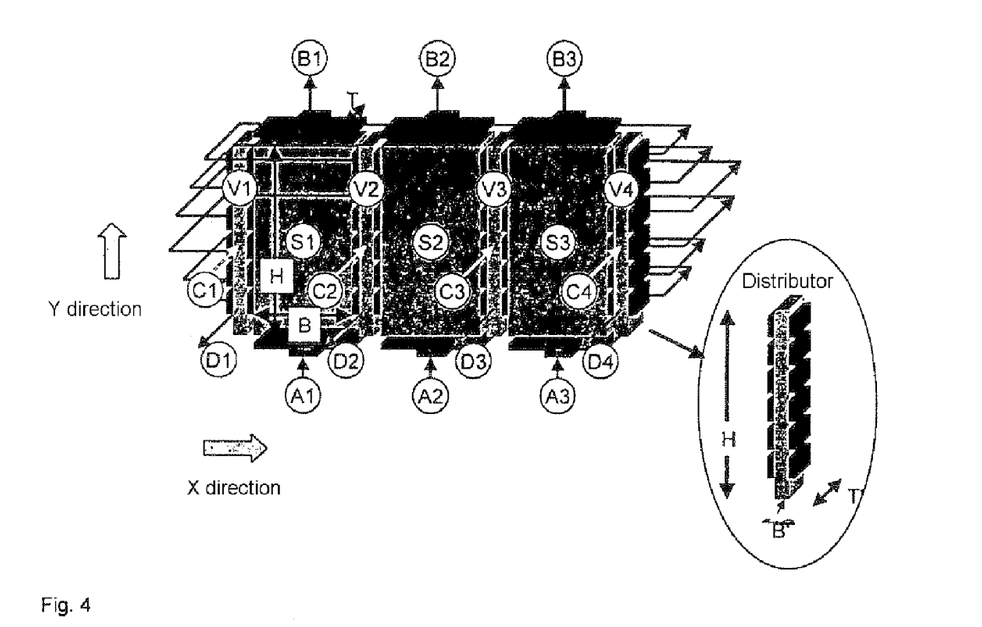
FIG. 4: Illustrates connections and construction

FIG. 4 shows a further illustration of the inventive apparatus with a total of three chromatographic columns. The connections are likewise indicated. The chromatographic columns $S_1$-$S_3$ have a square or part-ring shape, with width B, height H and depth T. In radial Y direction, the column inlets $A_1$-$A_3$ and column outlets $B_1$-$B_3$ can be found. At the column inlets, with the aid of a two-way valve, eluent or feed is supplied in each case. The column outlets $B_1$-$B_3$ are connected to the corresponding exit vessel by means of fractionating valves. In the case of a three-substance mixture with three vessels, three-way valves are suitable. Moreover, the distributors $V_1$-$V_4$ are present between the columns, in axial X direction. As in FIG. 3, the distributors divide the columns into G regions and are secured directly to the columns. FIG. 4 shows, by way of example, a division into six regions. In this case, the radial flow profile which arises in the case of flow-through in X direction is divided into regions which are collected by the distributors and distributed to the next column. At the same time, as detailed in the description of function, fresh solvent can be supplied through the connections $C_1$-$C_4$. In parallel thereto, a stream is drawn off via the particular connections $D_1$-$D_4$.

The distributors V* can, according to FIG. 3, be realized with the aid of switching valves, with the disadvantage that, as well as the enormous number of valves required, many connections with correspondingly high holdup volume also arise.

In a particular embodiment, the distributors V* are manufactured as a single compact component. Each distributor has to enable homogeneous flow-through without high pressure drops, and in particular it must not greatly disrupt the radial concentration profile. In each period during the radial injection phase (step 1), it should separate the chromatographic regions from one another (X direction closed). In the axial SMB separating phase (step 2), in contrast, it has to be possible to supply eluent into the circulation stream via a distributor. The return stream should be removed at the same point and possibly be used again. For the process according to the invention, all distributors V* have to fulfill these functions.

Figure 5:
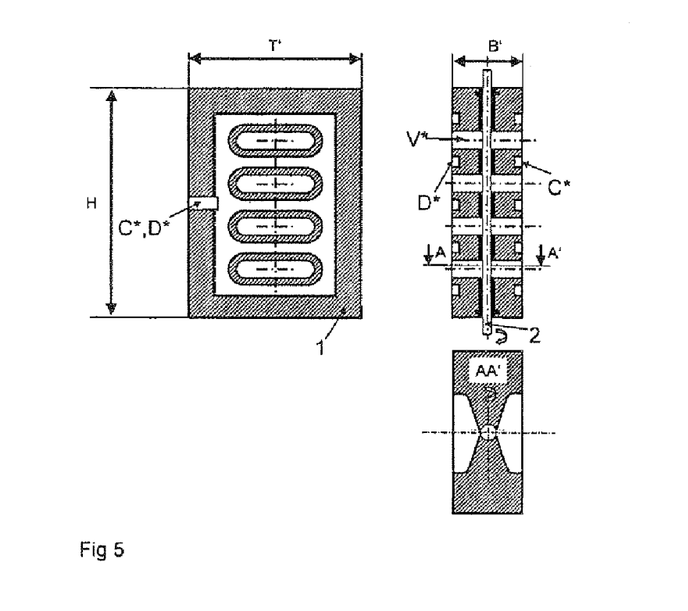
FIG. 5: Illustrates construction of the distributor

This has been achieved by the construction shown in FIG. 5. It consists of two components: a base body (1) and a rotating cylinder (2). Pathways for the eluent are milled into the distributor base body, each of which forms the distributor outlet D* and inlet C*. In axial direction, channels are provided in the base body, which are closed and opened by a rotating cylinder. In the cylinder (2), holes are namely found at the height of the channels of the base body (1). When the cylinder (2) is rotated, the channels in the base body (1) can be connected or interrupted. For this purpose, the channels narrow in the middle down to a cylindrical channel (see section AA'), which is blocked if required by the abovementioned closing mechanism.

EXAMPLES

Example 1

Simulation of the Separation of a Binary Substance Mixture

Figure 6:
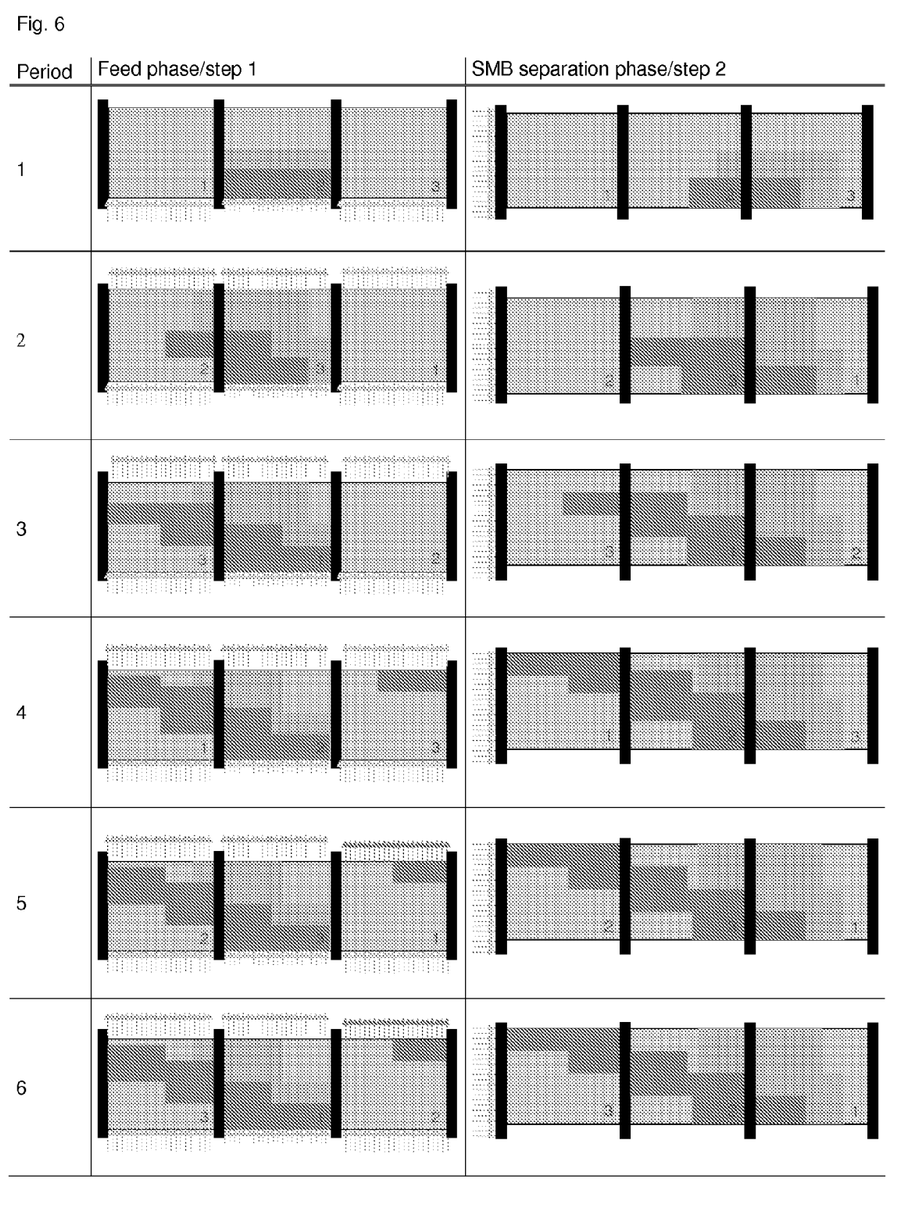
FIG. 6: Is a simulation of the novel process using the example of a two-substance mixture

FIG. 6 illustrates the way in which this process functions using the example of a two-substance mixture (A+B). Three chromatographic columns are used for this purpose. A linear adsorption with ideal behavior is assumed, i.e. without taking account of dispersion, diffusion or other front-smearing effects. Moreover, for the sake of simplicity, it is assumed that the readily adsorbable component (A) is twice as fast as the less adsorbable component (B). In addition, the volume flows in radial Y direction are adjusted equally over all columns ($Q_y$) and are half of the volume flow in axial X direction ($Q_x$). $Q_x$ in turn is selected such that the less adsorbable component (B), at the end of the second step, has migrated half a column length further overall. The example thus constructed shall, at this point, serve only for understanding of the individual steps and of the overall process.

In FIG. 6, it is possible to follow how the concentration profiles of the components A and B through the three chromatographic columns evolve in the course of six periods. In the first period (line 1 in FIG. 6), the feed is applied to the second column during the feed phase/step 1. Component A migrates up to the middle of the column, while component B loads one quarter of the column. In the SMB separation phase/step 2, the eluent flows in X direction. At the end of the first period, component A, both in X and in Y direction, is further away from component B, which is the result of the two-dimensional separation (line 1, column 2, FIG. 6). For period 2, step 1, the feed is now applied to the third column (line 2, column 1, FIG. 6). In this step, component A is obtained both at the outlet of the second and of the third column. Owing to its stronger adsorption, component B takes four periods to be removed at the outlet of the first column.

As can be taken from FIG. 6 overall, the two-substance mixture can be separated on the basis of these settings. Both components are removed separately at the particular upper outlets (Y direction) of the columns. Similarly to the conventional SMB process, a cyclic equilibrium is achieved here too. In this case, and assuming ideal behavior, it is established after exactly four periods. It is pointed out here that, in the simulation presented, only three chromatographic columns were used, which would not have been possible in the case of the conventional SMB process. In this novel process, even two columns are sufficient, which, however, is at the expense of low productivity.

Example 2

Separation of a Tertiary Substance Mixture

Figure 7:
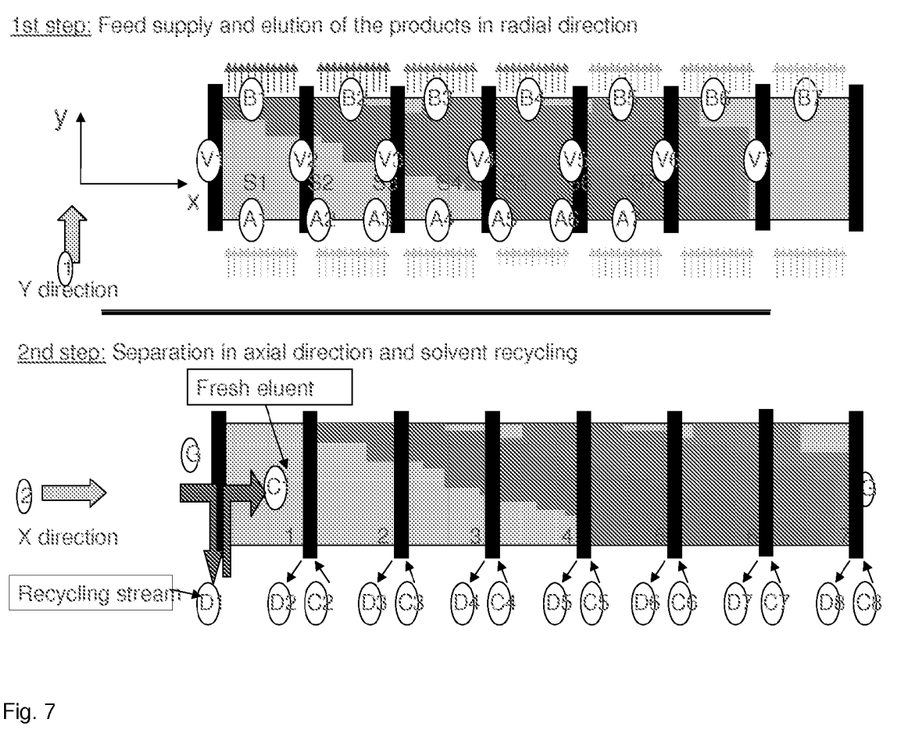
FIG. 7: Illustrates the principle of separation of a tertiary substance mixture
Figure 8:
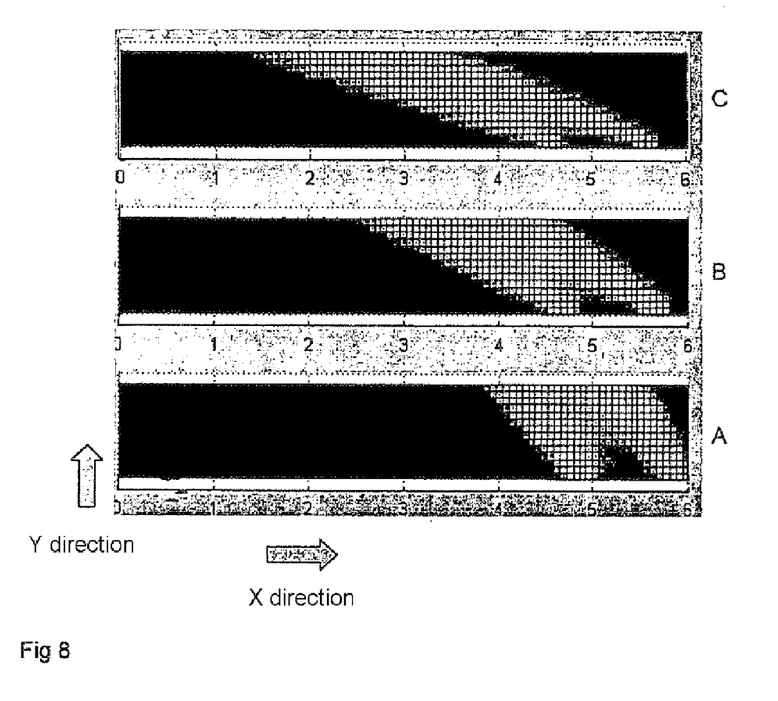
FIG. 8: Illustrates the concentration profile of the components A, B and C (study 1)

In the operation of this novel process, a distinction is drawn, as illustrated in FIG. 7 using the example of a ternary substance separation with a total of seven columns, between two steps which are performed in succession and form one period of the system. In the first step (=feed phase), feed is supplied in radial Y direction at one point ($A_4$) in the circuit, and otherwise pure solvent is supplied to the remaining columns ($A_1$-$A_3$, $A_5$-$A_7$). In this step, the distributors ($V_1$-$V_7$) separate the chromatographic columns ($S_1$-$S_7$) from one another, as a result of which the volume flow of each individual chromatographic column can be adjusted independently. The individual volume flows are established here such that the particular target component is obtained in the desired purity at the particular outlet ($B_1$-$B_7$) of the particular chromatographic column. The correct values for the volume flows are determined on the basis of a model-based design calculation or determined experimentally.

In the second phase (=SMB separation phase), separation is effected along the X direction by supplying fresh solvent at a distributor $V_1$ in the circuit through $C_1$. All further distributors $V_2$-$V_7$ are open in X direction. The overall concentration profile is conveyed in X direction. The volume flow of the SMB separation is adjusted such that, at the end of the period, the column charged with fresh eluent (column 1 here) is regenerated completely, i.e. only pure solvent leaves the column. At the distributor outlet D1, two situations can arise:

1. either pure solvent occurs, which can be recycled (recycling stream),
2. or the most easily adsorbable components occur, which are passed into the corresponding product vessel.

Whether one or the other operating mode arises depends on the selection of the volume flows and the adsorption properties of the components to be separated. A multicomponent detector can optionally be installed in the recycling stream in order to be able to switch to waste in the case of breakthrough of an undesired component.

As soon as the second step is complete, the period has ended and is followed by a new period. The feed points for feed and eluent in radial direction ($A_1$-$A_7$) and the feed outlets ($B_1$-$B_7$) are moved one column further in flow direction. According to FIG. 7, the feed supply is shifted from A4 to A5. The column discharges are connected correspondingly to the new product vessels. In axial direction, the eluent inlet is shifted from distributor inlet $C_1$ to $C_2$, and the eluent outlet from distributor outlet $D_1$ to $D_2$. As a result of this repeated relaying, a simulated countercurrent forms in axial X direction between the solid phase and the liquid.

This will be illustrated with reference to a ternary substance separation with the following substance properties.

The following study was performed with a unit according to FIG. 4 with distributor according to FIG. 5.

Substance Properties of a Ternary Mixture

| Parameter | Value | Description |
| --- | --- | --- |
| N [-] | 6 | Number of columns |
| $\epsilon_{ext}$ [-] | 0.4 | External porosity |
| B [cm] | 10 | Horizontal length of a column |
| H [cm] | 10 | Vertical length of a column |
| T [cm] | 2 | Depth of a column |
| $n_{sp}$ [-] | 3 | Number of components |
| $c_{fe}$ [g/l] | [2.5, 2.5, 2.5] | Feed concentration |
| A, B | [1e-4, 20] | Van-Deemter parameter |
| H [-] | [2.0, 1.5, 1.0] | Henry coefficients |
| Start feed | 2 | Position of the first feed supply |
| Duration of step 1 [s] | see studies | Duration of the feed injection |
| Duration of step 2 [s] | see studies | Duration of the SMB separation |
| $Q_{hor}$ [ml/min] | see studies | Horizontal volume flow |
| $Q_{ver}$ [ml/min] | see studies | Vertical volume flow |

The number of chromatographic columns is six. The first feed is applied to the second column (at $A_2$). The eluent supply takes place in step 2 of period 1 (X direction) at distributor 1 (through $C_1$).

Free operating parameters are the volume flows in axial and radial direction, which are varied in the following studies:

Study 1: Start feed position=5, $Q_{hor}$=15 ml/min, $Q_{ver}$=15 ml/min

FIG. 6 shows the two-dimensional concentration profile which arises for the particular components (A, B, C) at the end of the tenth period. The feed was just supplied to the penultimate column in position 5. Component A is the least adsorbable component, C the most strongly adsorbable component and B the intermediate component. The highly concentrated regions are dark red, while the pure solution is blue. It can be seen that the components migrate along different tracks.

Study 2: Start feed position=3, $Q_{hor}$=25 ml/min, $Q_{ver}$=15 ml/min

Figure 9:
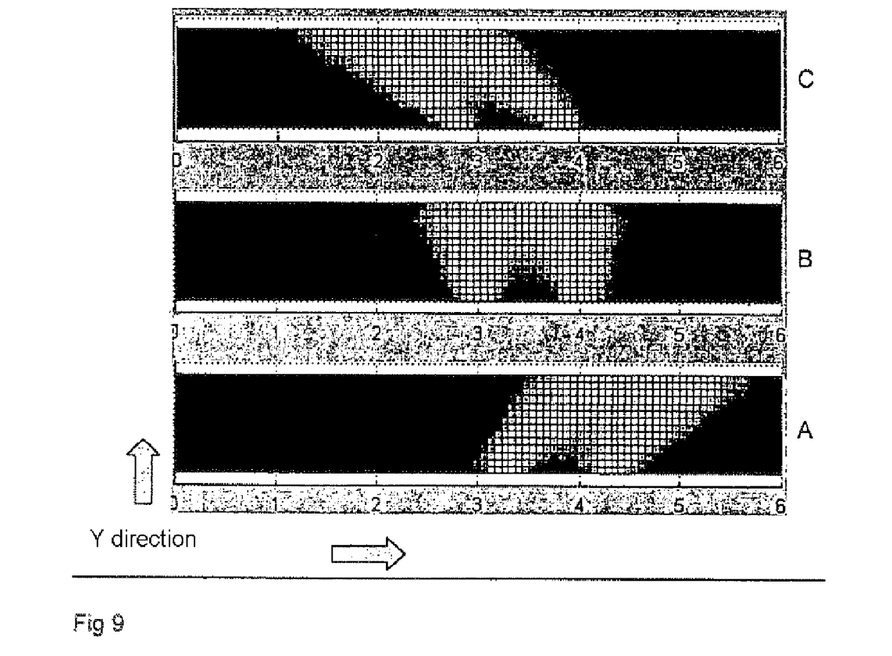
FIG. 9: Illustrates the concentration profile of the components A, B and C (study 2)

In this study, the horizontal volume flow was increased by 10 ml/min, such that the components are separated more strongly in axial X direction. The start feed position was simultaneously shifted from the fifth to the third column. The position of the transverse tracks, along which the components migrate, can be influenced by this controlled alteration of the axial volume flow and of the feed inlet point. This study has succeeded in allowing components A and C each to migrate to the right or left relative to the feed point, while the intermediate component B finds a straight-line path to the outlet. FIG. 9 shows the steady-state concentration profiles at the end of the tenth period.

The invention claimed is:

1. A chromatographic quasi-continuous process for separating binary and multisubstance mixtures in a unit formed of a plurality of individual columns bonded to one another in a direction X, wherein a two-dimensional separation is achieved by
   a in step 1 of a period p, supplying the feed in a column m and supplying an eluent stream in a direction Y to the other columns,
   b in step 2 of the period p, flowing an eluent stream through the bonded columns in the direction X and forming a circulation stream,
   c in step 1 of the period p+1, supplying further feed in the column m+1 and supplying further eluent stream in direction Y to the other columns,
   d in step 2 of the period p+1, again flowing an eluent stream through the bonded columns in the direction X and forming a circulation stream,
   e repeating a) to d) continuously.

2. The process as claimed in claim 1, wherein, in the second step, fresh solvent is supplied at a distributor inlet $C_j$ of a given distributor $V_n$, and the circulation stream is removed at a distributor outlet $D_j$ of the same distributor $V_n$.

3. The process as claimed in claim 1 wherein a separated component is obtained in a semicontinuous process at the column outlet B* and possibly additionally at the distributor outlet Dn in the axial direction X.

4. The process according to claim 1, wherein the circulation stream is established such that the column Sn is regenerated completely at the end of each period.

* * * * *